(12) United States Patent
Ebdrup et al.

(10) Patent No.: US 7,037,905 B2
(45) Date of Patent: May 2, 2006

(54) PHARMACEUTICAL USE OF BORONIC ACIDS AND ESTERS THEREOF

(75) Inventors: Soren Ebdrup, Roskilde (DK); Per Vedso, Frederiksberg (DK); Poul Jacobsen, Slangerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/614,233

(22) Filed: Jul. 7, 2003

(65) Prior Publication Data

US 2004/0053889 A1 Mar. 18, 2004

Related U.S. Application Data

(63) Continuation of application No. PCT/DK03/00315, filed on May 14, 2003.

(30) Foreign Application Priority Data

Jun. 14, 2002 (DK) .................................. 2002 00902

(51) Int. Cl.
*A61K 31/69* (2006.01)

(52) U.S. Cl. ......................................................... 514/64
(58) Field of Classification Search ................... 514/64
See application file for complete search history.

(56) References Cited

U.S. PATENT DOCUMENTS

| 5,312,816 | A | * | 5/1994 | Spielvogel et al. | ............ 514/64 |
| 6,075,014 | A | | 6/2000 | Weston et al. | ................ 514/64 |
| 6,267,952 | B1 | * | 7/2001 | Mandeville, III et al. | ....................... 424/78.08 |
| 2002/0128232 | A1 | * | 9/2002 | Henderson et al. | ........... 514/79 |
| 2003/0064963 | A1 | * | 4/2003 | Holmes-Farley et al. | ..... 514/64 |

FOREIGN PATENT DOCUMENTS

| EP | 792883 | 3/1997 |
| FR | 2758329 | 1/1997 |
| WO | WO 98/31688 A1 | 7/1998 |

* cited by examiner

*Primary Examiner*—Raymond J. Henley, III
(74) *Attorney, Agent, or Firm*—Rosemarie R. Wilk-Orescan; Reza Green; Richard W. Bork

(57) ABSTRACT

Use of compounds to inhibit hormone-sensitive lipase, the use of these compounds as pharmaceutical compositions, pharmaceutical compositions comprising the compounds, method of treatment employing these compounds and compositions, and novel compounds. The present compounds are inhibitors of hormone-sensitive lipase and may be useful in the treatment and/or prevention of a range of medical disorders where a decreased activity of hormone-sensitive lipase is desirable.

59 Claims, No Drawings

PHARMACEUTICAL USE OF BORONIC ACIDS AND ESTERS THEREOF

CROSS REFERENCE TO RELATED APPLICATIONS

This application is a continuation of international application PCT/DK03/00315, designating the United States, filed May 14, 2003, claiming priority to Danish application number PA 2002 00902, filed Jun. 14, 2002, the contents of each of which is hereby incorporated by reference herein in its entirety.

FIELD OF THE INVENTION

The present invention relates to use of compounds and pharmaceutical compositions containing them for treating medical disorders where it is desirable to modulate the activity of hormone-sensitive lipase.

BACKGROUND OF THE INVENTION

The overall energy homeostasis of a mammalian system requires a high degree of regulation to ensure the availability of the appropriate substrate at the appropriate time. Plasma glucose levels rise during the post-prandial state, to return to pre-prandial levels within 2–3 hours. During these 2–3 hours, insulin promotes glucose uptake by skeletal muscle and adipose tissue and decreases the release of free fatty acids (FFA) from adipocytes, to ensure that the two substrates do not compete with each other. When plasma glucose levels fall, an elevation in plasma FFA is necessary to switch from glucose to fat utilization by the various tissues.

In individuals with insulin resistance, FFA levels do not fall in response to insulin, as they do in normal individuals, preventing the normal utilization of glucose by skeletal muscle, adipose and liver. Furthermore, there is a negative correlation between insulin sensitivity and plasma FFA levels.

Hormone-sensitive lipase (HSL) is an enzyme, expressed primarily in adipocytes but also in adrenal gland, pancreatic β-cells, macrophages and testicles. HSL catalyses the hydrolysis of triglycerides to diglycerides and the subsequent hydrolysis of diglycerides and, to some extent, monoglycerides (Frederikson et al., 1981). It is through the regulation of this enzyme that the levels of circulating FFA are modulated. Insulin leads to the inactivation of HSL with a subsequent fall in plasma FFA levels during the postprandial state, followed by the activation of the enzyme when the insulin concentration falls and catecholamines rise during the post-absorptive period. The activation of HSL leads to an increase in plasma FFA, as they become the main source of energy during fasting.

The activation-inactivation of HSL is primarily mediated through the cAMP-protein kinase A and AMP-dependent kinase pathways. There are compounds like nicotinic acid and its derivatives, that decrease the activation of HSL via these pathways and cause a decrease in lipolysis that leads to a reduction in the FFA levels. These drugs have a beneficial effect in the utilization of glucose and in the normalization of the excess triglyceride synthesis seen in patients with elevated FFA. However, since these pathways are used by other processes in the body, these drugs have severe side effects.

Boronic acids and derivatives thereof have been shown to have a number of enzyme-inhibitory properties. Certain boronic acids have been shown to inhibit beta-lactamases and have antibacterial applications when combined with beta-lactam antibiotics (U.S. Pat. No. 6,075,014). WO 98/31688 discloses boronic acid derivatives claimed useful as angiogenesis inhibitors. FR 2,758,329 discloses (4(5-imidazolyl(butyl) boronic acid derivatives containing a 1,2-dihydro-2oxo-1-pyridinyl group, and their antithrombotic activity. EP 792883 discloses boronic acid derivative with are thrombin-inhibiting and trypsin-like serine protease-inhibiting. However, these references neither disclose nor suggest that boronic acids or derivatives thereof may have HSL inhibitory activity.

We have found boronic acids and esters thereof that specifically inhibit the lipolytic activity of HSL and lead to a decrease in plasma FFA levels. These compounds can be used to treat disorders where a decreased level of plasma FFA is desired, such as insulin resistance, syndrome X, dyslipidemia, abnormalities of lipoprotein metabolism.

One object of the present invention is to provide compounds and pharmaceutical compositions that inhibit the lipolytic activity of HSL. A further object is to provide compounds which have good pharmaceutical properties such as solubility, bioavailability etc.

Definitions

The following is a detailed definition of the terms used to describe the compounds of the invention.

"Halogen" designates an atom selected from the group consisting of F, Cl, Br and I.

The term "$C_{1-6}$-alkyl" in the present context designates a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkyl" in the present context designates a saturated, branched or straight hydrocarbon group having from 2 to 6 carbon atoms. Representative examples include, but are not limited to, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{1-6}$-alkoxy" in the present context designates a group —O—$C_{1-6}$-alkyl wherein $C_{1-6}$-alkyl is as defined above. Representative examples include, but are not limited to, methoxy, ethoxy, n-propoxy, isopropoxy, butoxy, isobutoxy, sec-butoxy, tert-butoxy, n-pentoxy, isopentoxy, neopentoxy, tert-pentoxy, n-hexoxy, isohexoxy and the like.

The term "$C_{1-6}$-alkylthio" in the present context designates a group —S—$C_{1-6}$-alkyl wherein $C_{1-6}$-alkyl is as defined above. Representative examples include, but are not limited to, methylthio, ethylthio, isopropylthio, n-propylthio, t-butylthio, n-pentylthio and the like.

The term "$C_{2-6}$-alkenyl" as used herein, represent an olefinically unsaturated branched or straight hydrocarbon group having from 2 to 6 carbon atoms and at least one double bond. Examples of such groups include, but are not limited to, vinyl, 1-propenyl, 2-propenyl, allyl, isopropenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The term "$C_{3-10}$-cycloalkyl" as used herein represents a saturated mono-, bi-, tri- or spirocarbocyclic group having from 3 to 10 carbon atoms. Representative examples are cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcaryl, adamantyl and the like.

The term "$C_{3-8}$-heterocyclyl" as used herein represents a saturated 3 to 8 membered ring containing one or more heteroatoms selected from nitrogen, oxygen and sulfur. Representative examples are pyrrolidyl, piperidyl, piperazinyl, morpholinyl, thiomorpholinyl, aziridinyl, tetrahydrofuranyl and the like.

The term "aryl" as used herein represents a carbocyclic aromatic ring system being either monocyclic, bicyclic, or polycyclic, such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "aryloxy" as used herein represents an aryl which is linked via an oxygen atom, e.g. phenoxy, 1-naphthyloxy, 2-naphthyloxy and the like.

The term "heteroaryl" as used herein represents a heterocyclic aromatic ring system containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, 3,4-dihydroisoquinolinyl, pyrrolinyl, pyrazolinyl, indolinyl, oxazolidinyl, oxazolinyl, oxazepinyl and the like.

The term "heterocyclic system" as used herein includes aromatic as well as non-aromatic ring moieties, which may be monocyclic, bicyclic or polycyclic, and containing in their ring structure one or more heteroatoms selected from nitrogen, oxygen and sulfur. Non-limiting examples of such heterocyclic systems are $C_{3-8}$-heterocyclyl and heteroaryl.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "optionally covalently bound" as used herein means that the substituents in question are either not covalently bound to each other or the substituents are directly connected to each other by a covalent bond. A non-limiting example of such optionally covalently bound substituents is —N-ethyl-n-propyl which provided that the substituents, ethyl and n-propyl, are optionally covalently bound may be —N-ethyl-n-propyl, 1-piperidyl, 3-methyl-1-pyrrolidyl or 2,3-dimethyl-1-azetidyl.

DETAILED DESCRIPTION OF THE INVENTION

One aspect of the present invention is the use of a boronic acid, an ester thereof, a prodrug thereof, or a pharmaceutically acceptable salt thereof, or a pharmaceutically acceptable solvate thereof for a) inhibition of the lipolytic activity of hormone-sensitive lipase against triacylglycerols, diacylglycerols, cholesterol acyl esters or steroid acyl esters; and/or b) modulating the plasma level of free fatty acids, glycerol, LDL-cholesterol, HDL-cholesterol, insulin and/or glucose; and/or c) modulating intracellular triacylglycerol and cholesterol ester stores, intracellular level of fatty acids, fatty acid esters such as diacylglycerols, phosphatidic acids, long chain acyl-CoA's as well as citrate or malonyl-CoA; and/or d) increasing insulin sensitivity in adipose tissue, skeletal muscle, liver or pancreatic β cells; and/or e) modulating insulin secretion from pancreatic β cells; and/or f) inhibition of male fertility in a patient.

In this application the term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

In this application the term "pharmaceutically acceptable" is defined as being suitable for administration to humans without adverse events.

In this application the term "prodrug" is defined as a chemically modified form of the active drug, said prodrug being administered to the patient and subsequently being converted to the active drug. Techniques for development of prodrugs are well known in the art.

A second aspect of the present invention is the use of a boronic acid, an ester thereof, a prodrug thereof, or a pharmaceutically acceptable salt thereof, or a pharmaceutically acceptable solvate thereof for the preparation of a medicament for the treatment of any disorder where it is desirable to a) inhibit the lipolytic activity of hormone-sensitive lipase against triacylglycerols, diacylglycerols, cholesterol acyl esters or steroid acyl esters; and/or b) modulate the plasma level of free fatty acids, glycerol, LDL-cholesterol, HDL-cholesterol, insulin and/or glucose; and/or c) modulate intracellular triacylglycerol and cholesterol ester stores, intracellular level of fatty acids, fatty acid esters such as diacylglycerols, phosphatidic acids, long chain acyl-CoA's as well as citrate or malonyl-CoA; and/or d) increase insulin sensitivity in adipose tissue, skeletal muscle, liver or pancreatic β cells; and/or e) modulate insulin secretion from pancreatic β cells; and/or f) inhibit male fertility in a patient.

In one embodiment $pK_a$ of said boronic acid, an ester thereof, a prodrug thereof or a pharmaceutically acceptable salt thereof is between 2.0 and 11.5, between 3.0 and 10.5, between 4.0 and 9.5, between 5.0 and 8.5, preferably between 5.5 to 8.0, and most preferable between 6.0 to 7.5.

In another embodiment the boronic acid, an ester thereof or a prodrug thereof is a dimer or trimer of a boronic acid.

In a further embodiment said dimer or trimer of a boronic acid comprises a structure selected from

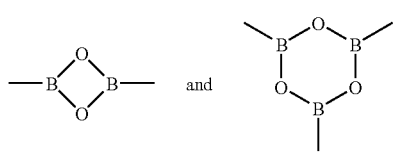

In another embodiment said boronic acid, an ester thereof or a prodrug thereof comprises an atom selected from the group consisting of S, P, I, Br, Si, Se and Ge.

In another embodiment said boronic acid, an ester thereof or a prodrug thereof is of the general formula I

wherein $R^1$ and $R^2$ are independently selected from hydrogen, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl;

wherein $R^2$ is optionally covalently bound to $R^1$ by one or two ether, thioether, O—B, C—C, C=C or C—N bonds, to form a ring system with the O-atoms to which $R^1$ and $R^2$ are bound; and $R^3$ is selected from $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-8}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl;

or any tautomeric forms, stereoisomers, mixture of stereoisomers including a racemic mixture, oligomers or polymorphs.

In another embodiment said boronic acid, an ester thereof, or a prodrug thereof, comprises a structure selected from the group consisting of

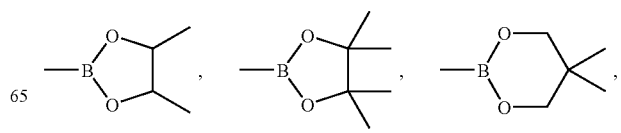

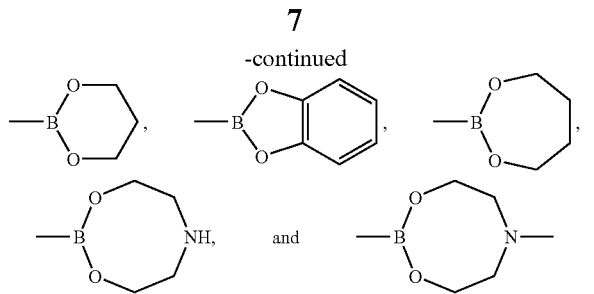

In another embodiment the group R³ in the general formula (I) comprises an optionally substituted moiety selected from the group consisting of pyrrolidine-2-yl, pyrrolidine-3-yl, pyrrole-2-yl, pyrrole-3-yl, 3H-pyrrole-2-yl, 3H-pyrrole-3-yl, 3H-pyrrole-4-yl, 3H-pyrrole-5-yl, oxolane-2-yl, oxolane-3-yl, furane-2-yl, furane-3-yl, thiolane-2-yl, thiolane-3-yl, thiophene-2-yl, thiophene-3-yl, pyrazole-3-yl, pyrazole-4-yl, pyrazole-5-yl, pyrazolidine-3-yl, pyrazolidine-4-yl, imidazole-2-yl, imidazole-4-yl, imidazole-5-yl, imidazolidine-2-yl, imidazolidine-4-yl, 3H-pyrazole-3-yl, 3-H-pyrazole-4-yl, 3H-pyrazole-5-yl, isoxazole-3-yl, isoxazole-4-yl, isoxazole-5-yl, oxazole-2-yl, oxazole-4-yl, oxazole-5-yl, isothiazole-3-yl, isothiazole-4-yl, isothiazole-5-yl, thiazole-2-yl, thiazole-4-yl, thiazole-5-yl, 1,2,5-oxadiazole-3-yl, 1,3,5-oxadiazole-2-yl, 1,3,5-oxadiazole-4-yl, 1,3,4-oxadiazole-2-yl, 1,2,3,5-oxatriazole-4-yl, 1,2,5-thiadiazole-3-yl, 1,3,5-thiadiazole-2-yl, 1,3,5-thiadiazole-4-yl, 1,3,4-thiadiazole-2-yl, 1,2,3,5-thiatriazole-4-yl, 1,2,3-triazole-4-yl, 1,2,3-triazole-5-yl, 1,2,4-triazole-3-yl, 1,2,4-triazole-5-yl, 1,2,5-triazole-3-yl, tetrazole-5-yl, 1,3-oxathiole-2-yl, 1,3-oxathiole-4-yl, 1,3-oxathiole-5-yl, benzofurane-2-yl, benzofurane-3-yl, isobenzofurane-1-yl, benzothiophene-2-yl, benzothiophene-3-yl, isobenzothiophene-1-yl, 1H-indole-2-yl, 1H-indole-3-yl, 2H-isoindole-1-yl, indolizine-1-yl, indolizine-2-yl, indolizine-3-yl, 1H-benzimidazole-2-yl, 1H-benzothiazole-2-yl, 1H-benzoxazole-2-yl, 1H-benzisooxazole-3-yl, 3H-indazole-3-yl, piperedine-1-yl, piperedine-2-yl, piperedine-3-yl, piperedine-4-yl, piperazine-1-yl, piperazine-2-yl, 2,5-dione-piparazine-1-yl, 2,5-dione-piparazine-3-yl and phenyl.

In another embodiment the group R³ is selected from the group consisting of

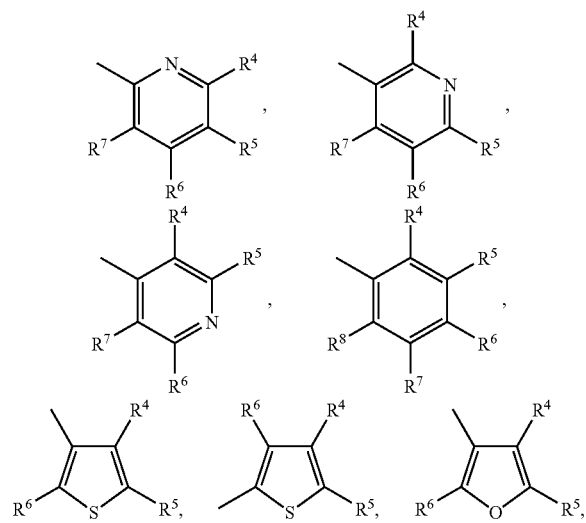

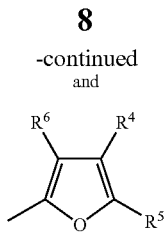

wherein R⁴, R⁵, R⁶, R⁷ and R⁸ are independently selected from $C_{1-6}$-alkyl, $C_{2-6}$-alkenyl $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl.

In another embodiment the molar weight of each of R⁴, R⁵, R⁶, R⁷ and R⁸ are below about 100 Dalton, preferably below about 80 Dalton, more preferable below 50 Dalton and even more preferable below about 20 Dalton.

In another embodiment R⁴, R⁵, R⁶, R⁷ and R⁸ are independently selected from hydrogen, halogen, hydroxyl, perhalomethyl, perhalomethoxy, $C_{1-6}$-alkyl, $C_{1-6}$-alkoxy and $C_{1-6}$-alkylthio.

In another embodiment R⁴, R⁵, R⁶, R⁷ and R⁵ are independently selected from hydrogen, halogen, methyl, methoxy, thiomethoxy, perhalomethyl, perhalomethoxy In another embodiment R⁴, R⁵, R⁶, R⁷ and R⁸ are independently selected from hydrogen, halogen, trifluoromethyl and trifluoromethoxy.

In another embodiment the group R¹ is H.

In another embodiment the group R¹ is H and the group R² is H.

In another embodiment said boronic acid, an ester thereof or a prodrug thereof is selected from the group consisting of
2-(5-Chlorothiophen-2-yl)-4,4,5,5-tetramethyl-[1,3,2] dioxaborolane,
2-(5-Chlorothiophen-2-yl)-5,5-dimethyl-[1,3,2] dioxaborinane,
2-(5-Chlorothiophen-2-yl)-[1,3,6,2]dioxazaborocane,
2-(3,5-Difluorophenyl)-[1,3,6,2]dioxazaborocane,
2-(3-Bromophenyl)-[1,3,6,2]dioxazaborocane,
2-(3-Chlorophenyl)-[1,3,6,2]dioxazaborocane,
2-(3-Fluorophenyl)-[1,3,6,2]dioxazaborocane,
2-(3-Trifluoromethylphenyl)-[1,3,6,2]dioxazaborocane,
2-(3,4,5-Trifluorophenyl)-[1,3,6,2]dioxazaborocane,
2-(3-Chlorophenyl)-5,5-dimethyl-[1,3,2]dioxaborinane,
5,5-Dimethyl-2-(3-trifluoromethylphenyl)-[1,3,2] dioxaborinane,
2-(5-Chloro-2-methoxyphenyl)-[1,3,6,2]dioxazaborocane,
2-(3-Trifluoromethoxyphenyl)-[1,3,6,2]dioxazaborocane,
2-(3,5-Dichlorophenyl)-[1,3,6,2]dioxazaborocane,
2-(3-Chloro-4-fluorophenyl)-[1,3,6,2]dioxazaborocane,
2-(4-Methylthiophen-2-yl)-[1,3,6,2]dioxazaborocane,
2-(3-Bromophenyl)-5,5-dimethyl-[1,3,2]dioxaborinane,
2-(5-Chloro-2-methoxyphenyl)-5,5-dimethyl-[1,3,2] dioxaborinane,
5,5-Dimethyl-2-(3,4,5-trifluorophenyl)-[1,3,2] dioxaborinane,
5,5-Dimethyl-2-(3-trifluoromethoxyphenyl)-[1,3,2] dioxaborinane,
2-(3,5-Dichlorophenyl)-5,5-dimethyl-[1,3,2]dioxaborinane,
2-(3-Chloro-4-fluorophenyl)-5,5-dimethyl-[1,3,2] dioxaborinane,
2-(3-Fluorophenyl)-5,5-dimethyl-[1,3,2]dioxaborinane,
5,5-Dimethyl-2-(4-methylthiophen-2-yl)-[1,3,2] dioxaborinane,
2-(3-Bromophenyl)-4,4,5,5-tetramethyl-[1,3,2] dioxaborolane,
2-(5-Chloro-2-methoxyphenyl)-4,4,5,5-tetramethyl-[1,3,2] dioxaborolane,
4,4,5,5-Tetramethyl-2-(3-trifluoromethoxyphenyl)-[1,3,2] dioxaborolane,
2-(3,5-Dichlorophenyl)-4,4,5,5-tetramethyl-[1,3,2] dioxaborolane,
2-(3-Chloro-4-fluorophenyl)-4,4,5,5-tetramethyl-[1,3,2] dioxaborolane,
2-(3-Chlorophenyl)-4,4,5,5-tetramethyl-[1,3,2] dioxaborolane,
4,4,5,5-Tetramethyl-2-(3-trifluoromethylphenyl)-[1,3,2] dioxaborolane,
4,4,5,5-Tetramethyl-2-(4-methylthiophen-2-yl)-[1,3,2] dioxaborolane,
4-Benzyloxyphenylboronic acid,
4-BROMOBENZENEBORONIC ACID N-METHYLDIETHANOLAMINE CYCLIC ESTER,
2-(3,5-DIFLUOROPHENYL)-5,5-DIMETHYL-1,3,2-DIOXABORINANE,3-BROMOBENZENEBORONIC ACID N-METHYLDIETHANOLAMINE CYCLIC ESTER,
2-(4-BROMOPHENYL)-5,5-DIMETHYL-1,3,2-DIOXABORINANE,
2-(2-chloroPHENYL)-5,5-DIMETHYL-1,3,2-DIOXABORINANE,
2-(5,5-Dimethyl-[1,3,2]dioxaborinan-2-yl)-benzonitrile,
2-(2-Fluoro-phenyl)-5,5-dimethyl-[1,3,2]dioxaborinane,
2-(5,5-Dimethyl-[1,3,2]dioxaborinan-2-yl)-benzoic acid ethyl ester,
5-CHLORO-2-METHOXYPHENYLBORONIC ACID,
3,5-Dibromophenylboronic acid,
3-Ethoxyphenylboronic acid,
3-phenylphenylboronic acid,
4-fluorophenylboronic acid,
2-Bromophenylboronic acid,
3-Bromophenylboronic acid,
2,6-Dichlorophenylboronic acid,
3-Methylphenylboronic acid,
2-Chlorophenylboronic acid,
3-Chlorophenylboronic acid,
3-(TRIFLUOROMETHOXY)BENZENEBORONIC ACID,
3-Trifluoromethylphenylboronic acid,
3,5-Bis(Trifluoromethyl)phenylboronic acid,
3,5-Dichlorophenylboronic acid,
3-Chloro-4-fluorophenylboronic acid,
3,5-Difluorophenylboronic acid,
3-Fluorophenylboronic acid,
2,3-DIFLUORO-4-PENTYLPHENYLBORONIC ACID,
(3-FLUORO-4-BENZYLOXYPHENYL)BORONIC ACID,
3,4,5-Trifluorophenylboronic acid,
2,3,5-Trichlorophenylboronic acid,
2,5-Dichlorophenylboronic acid,
2,3-Difluorophenylboronic acid,
2,5-Difluorophenylboronic acid,
4'-(4,4,5,5-TETRAMETHYL-1,3,2-DIOXABOROLAN-2-YL)ACETANILIDE,
3,4-Difluorophenylboronic acid,
2,3-Dichlorophenylboronic acid,
2,3-Difluoro-4-bromophenylboronic acid,
3-Fluoro-4-phenylboronic acid,
2-Methoxy5-fluorophenylboronic acid,
3,4-Dichlorophenylboronic acid,
5-INDOLYL BORONIC ACID,
3-Formylphenylboronic acid,
4-(N,N-DIMETHYLCARBAMOYL)PHENYLBORONIC ACID,
6-Methoxy-2-phenyl-hexahydro-pyrano[3,2-a][1,3,2] dioxaborinine-7,8-diol,
2-Fluoro-4-(5-pentyl-[1,3,2]dioxaborinan-2-yl)-benzoic acid,
4-(3-Iodo-phenoxymethyl)-2-phenyl-[1,3,2]dioxaborolane,
3'-(4,4,5,5-TETRAMETHYL-1,3,2-DIOXABOROLAN-2-YL)-2-trimethylsilylthiophen,
4'-(4,4,5,5-TETRAMETHYL-1,3,2-DIOXABOROLAN-2-YL)2-nitrothiophene,
1-BENZOTHIOPHEN-3-YLBORONIC ACID,
2-FORMYL-3-THIOPHENEBORONIC ACID,
2-THIEN-3-YL-1,3,2-BENZODIOXABOROLE,
3-Thiophenboronic acid,
2-(2-FORMYL-3-METHYLTHIEN-5-YL)-1,3,2-DIOXABORINANE,
4-METHYLTHIOPHENE-2-BORONIC ACID,
5-METHYLFURAN-2-BORONIC ACID,
5-Methylthiophene-2-boronic acid,
BENZO[B]FURAN-2-BORONIC ACID, Benzo[B]thiophene-2-boronic acid, Furan-2-boronic acid, 5-Chlorothiophene-2-boronic acid, 5-Cyanothiophene-2-boronic acid, 5-Acetylthiophene-2-boronic acid, Thiophene-2-boronic acid, 3-Bromothiophene-2-boronic acid and 5,5-Dimethyl-2-(3-iodothiophen-2-yl)-[1,3,2] dioxaborinane.

In another embodiment $R^3$ is characterized in $pK_a$ of the compound $R^3$-B(OH)$_2$ being between 2.0 and 11.5, between 3.0 and 10.5, between 4.0 and 9.5, between 5.0 and 8.5, preferably between 5.5 to 8.0, and most preferable between 6.0 to 7.5.

In another embodiment said boronic acid, an ester thereof or a prodrug thereof has a molar weight of no greater than 1000 D.

In another embodiment the molar weight of said boronic acid, an ester thereof or a prodrug thereof is less than 750 D, preferably less than 500 D, more preferable less than 350 D, more preferable less than 300 D, more preferable less than 250 D and even more preferable less than 200 D.

In another embodiment said boronic acid, an ester thereof or a prodrug thereof has an $IC_{50}$ value as determined by the assay 3190.2 or 3180.1 disclosed herein of less than 50 µM, preferably less than 5 µM, more preferable less than 500 nM and even more preferable less than 100 nM.

In another embodiment said boronic acid, an ester thereof or a prodrug thereof has a solubility in water at 25° C. and pH 2.0 of at least 0.5 mg/L, preferably at least 2.5 mg/L, more preferable at least 20 mg/L, even more preferable at least 200 mg/L and most preferable at least 2 g/L.

In another embodiment the administration of said boronic acid, an ester thereof or a prodrug thereof is by the oral, nasal, transdermal, pulmonal, or parenteral route.

A third aspect of the invention concerns a pharmaceutical composition for the use according to the first and second aspects of the invention, wherein said pharmaceutical composition comprises, as an active ingredient, a boronic acid, an ester thereof, a prodrug thereof, or a pharmaceutically acceptable salt thereof, or a pharmaceutically acceptable solvate thereof, together with a pharmaceutically acceptable carrier or diluent.

In one embodiment the pharmaceutical composition for the use according to the first and second aspects of the invention, wherein said pharmaceutical composition comprises, as an active ingredient, a boronic acid, an ester thereof or a prodrug thereof as defined in any of the above embodiments, or a pharmaceutically acceptable salt thereof, together with a pharmaceutically acceptable carrier or diluent.

In another embodiment the pharmaceutical composition is in unit dosage form, comprising from about 0.05 mg to about 2000 mg, preferably from about 0.1 to about 500 mg of the boronic acid, an ester thereof, a prodrug thereof or a pharmaceutically acceptable salt thereof or a pharmaceutically acceptable solvate thereof as defined in any one of the above embodiments.

In another embodiment the pharmaceutical composition is for oral, nasal, transdermal, pulmonal or parenteral administration.

In a fourth aspect the invention concerns a method of treating any disorder where it is desirable to inhibit the lipolytic activity of hormone-sensitive lipase against triacylglycerols, diacylglycerols, cholesterol acyl esters or steroid acyl esters, wherein said method comprises the use according to any one of the first, second or third aspects of the invention.

In a fifth aspect the invention concerns a method of treating any disorder where it is desirable to modulate the plasma level of free fatty acids or to modulate the handling, storage and oxidation of intracellular fatty acid and cholesterol, wherein said method comprises the use according to any one of the first, second or third aspects of the invention.

In one embodiment of the fourth and fifth aspects, said disorder is selected from the group consisting of insulin resistance, diabetes type 1, diabetes type 2, metabolic syndrome X, impaired glucose tolerance, hyperglycemia, dyslipidemia, obesity, abnormalities of lipoprotein metabolism and any combination thereof.

In another aspect the invention concerns a method for the treatment of a patient suffering from insulin resistance, diabetes type 1, diabetes type 2, metabolic syndrome X, impaired glucose tolerance, hyperglycemia, dyslipidemia, hyperlipoproteinemia, hypertriglyceridemia, hyperlipidemia, hypercholesterolemia, or other abnormalities of lipoprotein metabolism, said method comprising administering to the patient a pharmaceutically effective amount of a boronic acid, an ester thereof, a prodrug thereof or a pharmaceutically acceptable salt thereof or a pharmaceutically acceptable solvate thereof.

In one embodiment said boronic acid or an ester thereof, or a prodrug thereof is a compound according to any one of the first, second or third aspects of the invention.

In another embodiment the patient is treated with said boronic acid, an ester thereof, a prodrug thereof or a pharmaceutically acceptable salt thereof or a pharmaceutically acceptable solvate thereof for at least about 1 week, for at least about 2 weeks, for at least about 4 weeks, for at least about 2 months or for at least about 4 months.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of disorders where a decreased level of plasma FFA is desirable, such as the conditions mentioned above.

In another aspect, the present invention relates to a method of treating and/or preventing type 2 diabetes, insulin resistance, metabolic syndrome X, impaired glucose tolerance, dyslipidemia and abnormalities of lipoprotein metabolism.

In a still further aspect, the present invention relates to the use of one or more compounds of the general formula I, or pharmaceutically acceptable salts thereof, for the preparation of a pharmaceutical composition for the treatment and/or prevention of type 2 diabetes, insulin resistance, metabolic syndrome X, impaired glucose tolerance, dyslipidemia and abnormalities of lipoprotein metabolism.

In a still further aspect, the present compounds are useful for the delaying or prevention of the progression from impaired glucose tolerance to type 2 diabetes.

In a still further aspect, the present compounds are useful for the delaying or prevention of the progression from non-insulin requiring type 2 diabetes to insulin requiring type 2 diabetes.

In another aspect, the present compounds reduce triglyceride levels and are accordingly useful for the treatment and/or prevention of ailments and disorders such as diabetes and/or obesity.

In still another aspect, the present compounds are useful for the treatment and/or prophylaxis of insulin resistance, impaired glucose tolerance, dyslipidemia, disorders related to metabolic syndrome X such as hypertension, obesity, insulin resistance, hyperglycaemia, atherosclerosis, hyperlipidemia, coronary artery disease, myocardial ischemia and other cardiovascular disorders.

In a still further aspect, the present compounds are useful for the delaying or prevention of the progression from impaired glucose tolerance to type 2 diabetes.

In a still further aspect, the present compounds are useful for the delaying or prevention of the progression from non-insulin requiring type 2 diabetes to insulin requiring type 2 diabe tes.

In another aspect, the present compounds reduce triglyceride levels and are accordingly useful for the treatment and/or prevention of ailments and disorders such as diabetes and/or obesity.

In still another aspect, the compounds of the present invention are useful for the treatment of hyperglycemia, elevated $HbA_{1c}$ level, hyperinsulinemia, type 1.5 diabetes, latent autoimmune diabetes in adults, maturity onset diabetes, beta-cell apoptosis, hemochromatosis induced diabetes, impaired glucose tolerance, impaired fasting glucose, metabolic syndrome X, insulin resistance, impaired lipid tolerance, cystic fibrosis related diabetes, polycystic ovarian syndrome, and gestational diabetes.

In still another aspect, the compounds of the present invention are useful for the treatment of obesity, dyslipidemia, diabetic dyslipidemia, hyperlipidemia, hypertriglyceridemia, hyperlipoproteinemia, hypercholesterolemia, hypertension, essential hypertension, acute hypertensive emergency, arteriosclerosis, atherosclerosis, restenosis, intermittent claudication (atherosclerosis oblitterens), cardiovascular disease, cardiomyopathy, cardiac hypertrophy, left ventricular hypertrophy, coronary artery disease, early coronary artery disease, heart insufficiency, exercise tolerance, chronic heart failure, mild chronic heart failure, arrhythmia, cardiac dysrythmia, syncopy, heart attack, myocardial infarction, Q-wave myocardial infarction, stroke, acute coronary syndrome, angina pectoris, unstable angina, cardiac bypass reocclusion, diastolic dysfunction, systolic dysfunction, non-Q-wave cardiac necrosis, catabolic changes after surgery, acute pancreatitis, and irritable bowel syndrome In still another aspect, the compounds of the present invention may be useful for the treatment of diabetic retinopathy, background retinopathy, preproliferative retinopathy, proliferative retinopathy, macular edema, cataracts, nephropathy, nephrotic syndrome, diabetic nephropathy, microalbuminuria, macroalbuminuria, neuropathy, diabetic neuropathy, distal symmetrical sensorimotor polyneuropathy, and diabetic autonomic neuropathy.

In still another aspect, the compounds of the present invention are useful for increasing the number of beta-cells in a patient, increasing the size of beta-cells in a patient or stimulating beta-cell proliferation, modulating beta-cell function and insulin secretion in a patient in need thereof, which method comprises administration of an effective amount of a compound of formula I to a patient in need thereof.

The compounds of the invention are also believed to be useful for reducing body weight in a patient in need thereof.

The compounds of the invention are also believed to be useful for weight neutral treatment of above mentioned diseases.

The compounds of the invention are also believed to be useful for redistributing fat in a patient in need thereof.

The compounds of the invention are also believed to be useful for redistributing central fat in a patient in need thereof.

The compounds of the invention are also believed to be useful for reducing or preventing central obesity.

The compounds of the invention are also believed to be useful for reducing postprandial serum lipid excursions.

The compounds of the invention are also believed to be useful for the treatment of fatty acid oxidation disorders such as MCAD.

In still another aspect, the compounds of the present invention are believed to be useful for the treatment of a disease, condition or disorder wherein cholesterol is a precursor. Such diseases, conditions or disorders may relate to testosterone, e.g. male contraception, excessive testosterone levels, PCOS and prostate cancer. They may also relate to cortisol or corticotropin, e.g. Cushing disease.

The compounds of the invention are also believed to be useful for the treatment of cancer. Thus, the compounds of the the the present invention may be useful for the treatment of insulinoma (pancreatic islet cell tumors), e.g. malignant insulinomas and multiple insulinomas, adipose cell carcinomas, e.g. lipocarconoma.

The compounds of the invention are also believed to be useful for the treatment of phaechromocytoma and other diseases with increased catecholamine incretion.

The compounds of the invention are also believed to be useful for the treatment of prostate cancer, e.g. adenocarcinoma.

In still another aspect, the compounds of the present invention may be useful for the treatment of hepatic steatosis.

In still another aspect, the compounds of the present invention may be useful for the treatment of cirrhosis.

In still another aspect, the compounds of the present invention may be useful for the treatment of AIDS or an AIDS related diseases, condition or disorders In still another aspect, the compounds of the present invention may be useful for the treatment of lipodystrophy In still another aspect, the compounds of the present invention may be useful for the treatment of lactic acidosis.

In yet another aspect, the compounds of the present invention are expected to be useful for the treatment of CNS diseases, conditions or disorders.

Thus, the compound of the present invention may be used for the treatment of Parkinsons disease, Alzheimers disease, ADHD (Attention Deficit Hyperactivity Disorder), feeding disorders such as bulimia and anorexia, depression, anxiety, cognitive memory disorders, age related cognitive decline, mild cognitive impairment and schizophrenia.

In yet another aspect, the compounds of the present invention may be useful for the treatment of inflammatory disorders, e.g. rheumatoid arthritis, psoriasis, systemic inflammatory response syndrome, sepsis and the like.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. meflormin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to processes according to reaction schemes $P_1$ and $P_2$ for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions.

The compounds of the invention may be administered alone or in combination with pharma-ceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

The therapeutic dose of the compound will depend upon the frequency and mode of administration, the sex, age, weight and general condition of the subject treated, the nature and severity of the condition treated and any concomitant diseases to be treated and other factors evident to those skilled in the art. The formulations may conveniently be presented in unit dosage form by methods known to those skilled in the art. In one embodiment the composition in unit dosage form, comprises from about 0.05 to about 2000 mg, preferably from about 0.1 to about 500 mg of the compound of formula I pharmaceutically acceptable salt thereof.

In a still further embodiment the pharmaceutical composition is for oral, nasal, transdermal, pulmonal, or parenteral administration.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the compound with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | q.s. |
| Coating: | |
| HPMC approx. | 9 mg |
| *Mywacett 9–40 T approx. | 0.9 mg |

*Acylated monoglyceride used as plasticizer for film coating.

The compounds of the invention may be administered to a patient which is a mammal, especially a human in need thereof. Such mammals include also animals, both domestic animals, e.g. household pets, and non-domestic animals such as wildlife.

In a further aspect of the invention the present compounds may be administered in combination with further pharmacologically active substances e.g. an antidiabetic or other pharmacologically active material, including other compounds for the treatment and/or prevention of insulin resistance and diseases, wherein insulin resistance is the pathophysiological mechanism.

Furthermore, the compounds according to the invention may be administered in combination with antiobesity agents or appetite regulating agents.

EXAMPLES

General Procedure (A)

The arylboronic acid (1 mmol) and the diol (1.1 mmol) in toluene (10 mL) were stirred at room temperature for 2 h. The organic phases was washed with water three times and subsequently evaporated and dried in vacuo.

General Procedure (B)

The arylboronic acid (1 mmol) and diethanolamine (1.1 mmol) in toluene (10 mL) were stirred at room temperature for 2 h. The solution was evaporated to dryness and the resulting crystals were washed with heptane/iso-propanol (1:9) and dried in vacuo.

Example 1

General Procedure (A)

2-(5-Chlorothiophen-2-yl)-4,4,5,5-tetramethyl-[1,3,2]dioxaborolane

The title compound (50%, oil) was prepared from 5-chlorothiophen-2-boronic acid and pinacol.

$^1$H NMR (300 MHz, CDCl$_3$): δ 1.32 (s, 12H), 6.96 (d, 1H), 7.40 (d, 1H).

Example 2

General Procedure (A)

2-(5-Chlorothiophen-2-yl)-5,5-dimethyl-[1,3,2]dioxaborinane

The title compound (54%, crystals) was prepared from 5-chlorothiophen-2-boronic acid and neopentylglycol.

$^1$H NMR (300 MHz, CDCl$_3$): δ 1.04 (s, 6H), 3.74 (s, 4H), 6.95 (d, 1H), 7.32 (d, 1H).

Example 3

General Procedure (B)

2-(5-Chlorothiophen-2-yl)-[1,3,6,2]dioxazaborocane

The title compound (28%, crystals) was prepared from 5-chlorothiophen-2-boronic acid and diethanolamin.

Mp 188–190° C. $^1$H NMR (300 MHz, DMSO d$_6$): δ 2.82–2.92 (m, 2H), 3.01–3.15 (m, 2H), 3.71–3.88 (m, 4H), 6.81 (d, 1H), 6.93 (d, 1H), 7.09 (bs, 1H).

Example 4

General Procedure (B)

2-(3,5-Difluorophenyl)-[1,3,6,2]dioxazaborocane

The title compound (93%, crystals) was prepared from 3,5-difluorophenylboronic acid and diethanolamin.

Mp 198–200° C. $^1$H NMR (300 MHz, DMSO d$_6$): δ 2.76–2.84 (m, 2H), 3.18–3.30 (m, 2H), 3.92–4.10 (m, 4H), 6.64 (tt, 1H), 6.82 (bs, 1H), 7.05–7.12 (m, 1H).

Example 5

General Procedure (B)

2-(3-Bromophenyl)-[1,3,6,2]dioxazaborocane

The title compound (78%, crystals) was prepared from 3-bromophenylboronic acid and diethanolamin.

Mp 208–212° C. $^1$H NMR (300 MHz, CDCl$_3$): δ 2.76–2.86 (m, 2H), 3.18–3.31 (m, 2H), 3.94–4.10 (m, 4H), 4.68 (bs, 1H), 7.18(t, 1H), 7.38 (dt, 1H), 7.49 (m, 1H), 7.69 (bs, 1H).

Example 6

General Procedure (B)

2-(3-Chlorophenyl)-[1,3,6,2]dioxazaborocane

The title compound (79%, crystals) was prepared from 3-chlorophenylboronic acid and diethanolamin.

Mp 235–238° C. $^1$H NMR (300 MHz, CDCl$_3$): δ 2.68–2.77 (m, 2H), 3.12–3.27 (m, 2H), 3.86–4.02 (m, 4H), 4.98 (bs, 1H), 7.22(d, 2H), 7.42 (t, 1H), 7.52 (bs, 1H).

Example 7

General Procedure (B)

2-(3-Fluorophenyl)-[1,3,6,2]dioxazaborocane

The title compound (79%, crystals) was prepared from 3-fluorophenylboronic acid and diethanolamin.

Mp 207–209° C. $^1$H NMR (300 MHz, CDCl$_3$): δ 2.68–2.78 (m, 2H), 3.12–3.27 (m, 2H), 3.85–4.02 (m, 4H), 4.97 (bs, 1H), 6.89–6.98 (m, 1H), 7.21–7.31 (m, 3H).

Example 8

General Procedure (B)

2-(3-Trifluoromethylphenyl)-[1,3,6,2]dioxazaborocane

The title compound (79%, crystals) was prepared from 3-trifluoromethylphenylboronic acid and diethanolamin.

Mp 188–192° C. $^1$H NMR (300 MHz, CDCl$_3$): δ 2.77–2.88 (m, 2H), 3.20–3.33 (m, 2H), 3.95–4.11 (m, 4H), 4.68 (bs, 1H), 7.40 (t, 2H), 7.52 (d, 1H), 7.77 (d, 1H), 7.84 (bs, 1H).

Example 9

General Procedure (B)

2-(3,4,5-Trifluorophenyl)-[1,3,6,2]dioxazaborocane

The title compound (70%, crystals) was prepared from 3,4,5-trifluorophenylboronic acid and diethanolamin.

Mp 265–269° C. $^1$H NMR (300 MHz, CDCl$_3$): δ 2.90–2.99 (m, 2H), 3.26–3.39 (m, 2H), 4.03–4.21 (m, 4H), 7.16(t, 2H).

Example 10

General Procedure (A)

2-(3-Chlorophenyl)-5,5-dimethyl-[1,3,2]dioxaborinane

The title compound (65%, crystals) was prepared from 3-chlorophenylboronic acid and neopentylglycol.

Mp 80–83° C. $^1$H NMR (300 MHz, CDCl$_3$): δ 1.03 (s, 6H), 3.78 (s, 4H), 7.27 (t, 1H), 7.39 (ddd, 1H), 7.66 (d, 1H), 7.77 (bs, 1H).

Example 11

General Procedure (A)

5,5-Dimethyl-2-(3-trifluoromethylphenyl)-[1,3,2]dioxaborinane

The title compound (58%, crystals) was prepared from 3-trifluoromethylphenylboronic acid and neopentylglycol.

Mp 80–83° C. $^1$H NMR (300 MHz, CDCl$_3$): δ 1.03 (s, 6H), 3.79 (s, 4H), 7.46 (t, 1H), 7.57 (d, 1H), 7.97 (d, 1H), 8.07 (bs, 1H).

Example 12

General Procedure (B)

2-(5-Chloro-2-methoxyphenyl)-[1,3,6,2]dioxazaborocane

The title compound (47%, crystals) was prepared from 5-chloro-2-methoxyphenylboronic acid and diethanolamin.

Mp 183–188° C. $^1$H NMR (300 MHz DMSO d$_6$): δ 2.73–2.85 (m, 2H), 3.12–3.27 (m, 2H), 3.59–3.70 (m, 2H), 3.68 (s, 3H), 3.76–3.85 (m, 2H), 6.79 (d, 2H), 7.14 (dd, 1H), 7.29 (d, 1H).

Example 13

General Procedure (B)

2-(3-Trifluoromethoxyphenyl)-[1,3,6,2]dioxazaborocane

The title compound (86%, crystals) was prepared from 3-trifluoromethoxyphenylboronic acid and diethanolamin.

Mp 130–136° C. $^1$H NMR (300 MHz DMSO d$_6$): δ 2.83–2.92 (m, 2H), 3.04–3.17 (m, 3H), 3.56–3.91 (m, 4H), 7.00 (bs, 1H), 7.11 (d, 1H), 7.28–7.36 (m, 2H), 7.43 (d, 1H).

Example 14

General Procedure (B)

2-(3,5-Dichlorophenyl)-[1,3,6,2]dioxazaborocane

The title compound (94%, crystals) was prepared from 3,5-dichlorophenylboronic acid and diethanolamin.

Mp 238–242° C. $^1$H NMR (300 MHz DMSO d$_6$): δ 2.85–2.92 (m, 2H), 3.06–3.18 (m, 2H), 3.76–3.90 (m, 4H), 7.07 (bs, 1H), 7.33 (s, 3H).

Example 15

General Procedure (B)

2-(3-Chloro-4-fluorophenyl)-[1,3,6,2]dioxazaborocane

The title compound (87%, oil) was prepared from 3-chloro-4-fluorophenylboronic acid and diethanolamin.

$^1$H NMR (300 MHz DMSO d$_6$): δ 2.83–2.91 (m, 2H), 3.04–3.17 (m, 2H), 3.75–3.90 (m, 4H), 6.98 (bs, 1H), 7.20 (dd, 1H), 7.34–7.40 (m, 1H), 7.48 (dd, 1H).

Example 16

General Procedure (B)

2-(4-Methylthiophen-2-yl)-[1,3,6,2]dioxazaborocane

The title compound (88%, oil) was prepared from 4-methylthiophen-2-boronic acid and diethanolamin.

¹H NMR (300 MHz DMSO d₆): δ 2.18 (s, 3H), 2.78–2.87 (m, 2H), 3.00–3.12 (m, 2H), 3.72–3.87 (m, 4H), 6.80 (s, 1H), 6.92 (s, 1H), 6.98 (bs, 1H).

Example 17

General Procedure (A)

2-(3-Bromophenyl)-5,5-dimethyl-[1,3,2]dioxaborinane

The title compound (86%, crystals) was prepared from 3-bromophenylboronic acid and neopentylglycol.

¹H NMR (300 MHz, CDCl₃): δ1.02 (s, 6H), 3.78 (s, 4H), 7.22 (t, 1H), 7.54 (dd, 1H), 7.70 (d, 1H), 7.93 (bs, 1H).

Example 18

General Procedure (A)

2-(5-Chloro-2-methoxyphenyl)-5,5-dimethyl-[1,3,2]dioxaborinane

The title compound (86%, oil) was prepared from 5-chloro-2-methoxyphenylboronic acid and neopentylglycol.

¹H NMR (300 MHz, CDCl₃): δ 1.04 (s, 6H), 3.79 (s, 4H), 3.81 (s, 3H), 6.79 (d, 1H), 7.30 (dd, 1H), 7.60 (d, 1H).

Example 19

General Procedure (A)

5,5-Dimethyl-2-(3,4,5-trifluorophenyl)-[1,3,2]dioxaborinane

The title compound (34%, yellow oil) was prepared from 3,4,5-trifluorophenylboronic acid and neopentylglycol.

¹H NMR (300 MHz, CDCl₃): δ 1.01 (s, 6H), 3.77 (s, 4H), 7.38 (t, 3H).

¹H NMR (300 MHz DMSO d₆): δ 2.78–2.87 (m, 2H), 3.00–3.12 (m, 2H), 3.72–3.87 (m, 4H), 6.80 (s, 1H), 6.92 (s, 1H), 6.98 (bs, 1H).

Example 20

General Procedure (A)

5,5-Dimethyl-2-(3-trifluoromethoxyphenyl)-[1,3,2]dioxaborinane

The title compound (64%, oil) was prepared from 3-trifluoromethoxyphenylboronic acid and neopentylglycol.

¹H NMR (300 MHz, CDCl₃): δ 1.03 (s, 6H), 3.78 (s, 4H), 7.26 (bd, 1H), 7.38 (t, 1H), 7.62 (bs, 1H), 7.71 (d, 1H).

Example 21

General Procedure (A)

2-(3,5-Dichlorophenyl)-5,5-dimethyl-[1,3,2]dioxaborinane

The title compound (80%, crystals) was prepared from 3,5-dichlorophenylboronic acid and neopentylglycol.

¹H NMR (300 MHz, CDCl₃): δ 1.03 (s, 6H), 3.77 (s, 4H), 7.40 (t, 1H), 7.63 (d, 2H).

Example 22

General Procedure (A)

2-(3-Chloro-4-fluorophenyl)-5,5-dimethyl-[1,3,2]dioxaborinane

The title compound (80%, crystalsl) was prepared from 3-chloro-4-fluorophenylboronic acid and neopentylglycol.

¹H NMR (300 MHz, CDCl₃): δ 1.03 (s, 6H), 3.77 (s, 4H), 7.10 (dd, 1H), 7.65 (dd, 1H), 7.82 (dd, 1H).

Example 23

General Procedure (A)

2-(3-Fluorophenyl)-5,5-dimethyl-[1,3,2]dioxaborinane

The title compound (55%, oil) was prepared from 3-trifluorophenylboronic acid and neopentylglycol.

¹H NMR (300 MHz, CDCl₃): δ 1.02 (s, 6H), 3.78 (s, 4H), 7.09 (dt, 1H), 7.28–7.36 (m, 1H), 7.46 (dd, 1H), 7.56 (d, 1H).

Example 24

General Procedure (A)

5,5-Dimethyl-2-(4-methylthiophen-2-yl)-[1,3,2]dioxaborinane

The title compound (60%, yellow crystals) was prepared from 4-methylthiophen-2-boronic acid and neopentylglycol.

¹H NMR (300 MHz, CDCl₃): δ 1.03 (s, 6H), 2.28 (s, 3H), 3.77 (s, 4H), 7.13 (d, 1H), 7.37 (d, 1H).

Example 25

General Procedure (A)

2-(3-Bromophenyl)-4,4,5,5-tetramethyl-[1,3,2]dioxaborolane

The title compound (77%, oil) was prepared from 3-bromophenylboronic acid and pinacol.

¹H NMR (300 MHz, CDCl₃): δ 1.35 (s, 12H), 7.23 (t, 1H), 7.58 (dd, 1H), 7.70 (d, 1H), 7.93 (bs, 1H).

Example 26

General Procedure (A)

2-(5-Chloro-2-methoxyphenyl)-4,4,5,5-tetramethyl-[1,3,2]dioxaborolane

The title compound (57%, oil) was prepared from 5-chloro-2-methoxyphenylboronic acid and pinacol.

¹H NMR (300 MHz, CDCl₃): δ 1.35 (s, 12H), 3.81 (s, 3H), 6.86 (d, 1H), 7.38 (dd, 1H), 7.80 (d, 1H).

Example 27

General Procedure (A)

4,4,5,5-Tetramethyl-2-(3-trifluoromethoxyphenyl)-[1,3,2]dioxaborolane

The title compound (25%, oil) was prepared from 3-trifluoromethoxyphenylboronic acid and pinacol.

¹H NMR (300 MHz, CDCl₃): δ 1.35 (s, 12H), 7.30 (d, 1H), 7.40 (t, 1H), 7.64 (bs, 1H), 7.72 (d, 1H).

Example 28

General Procedure (A)

2-(3,5-Dichlorophenyl)-4,4,5,5-tetramethyl-[1,3,2]dioxaborolane

The title compound (73%, oil) was prepared from 3,5-dichlorophenylboronic acid and pinacol.

Example 29
General Procedure (A)
2-(3-Chloro-4-fluorophenyl)-4,4,5,5-tetramethyl-[1,3,2]dioxaborolane The title compound (77%, oil) was prepared from 3-chloro-4-fluorophenylboronic acid and pinacol.

$^1$H NMR (300 MHz, CDCl$_3$): δ 1.34 (s, 12H), 7.12 (dd, 1H), 7.67 (ddd, 1H), 7.86 (dd, 1H).

Example 30
General Procedure (A)
2-(3-Chlorophenyl)-4,4,5,5-tetramethyl-[1,3,2]dioxaborolane The title compound (75%, oil) was prepared from 3-chlorophenylboronic acid and pinacol.

$^1$H NMR (300 MHz, CDCl$_3$): δ 1.36 (s, 12H), 7.30 (t, 1H), 7.42 (dt, 1H), 7.68 (d, 1H), 7.78 (bd, 1H).

Example 31
General Procedure (A)
4,4,5,5-Tetramethyl-2-(3-trifluoromethylphenyl)-[1,3,2]dioxaborolane The title compound (47%, oil) was prepared from 3-trifluoromethylphenylboronic acid and pinacol.

$^1$H NMR (300 MHz, CDCl$_3$): δ 1.35 (s, 12H), 7.48 (t, 1H), 7.70 (d, 1H), 7.97 (d, 1H), 8.06 (bs, 1H).

Example 32
General Procedure (A)
4,4,5,5-Tetramethyl-2-(4-methylthiophen-2-yl)-[1,3,2]dioxaborolane The title compound (54%, oil) was prepared from 4-methylthiophen-2-yl-boronic acid and pinacol.

$^1$H NMR (300 MHz, CDCl$_3$): δ 1.34 (s, 12H), 2.29 (s, 3H), 7.20 (s, 1H), 7.44 (s, 1H).

Example 33
Commercially Available Compound
4-Benzyloxyphenylboronic acid

Example 34
Commercially Available Compound
4-BROMOBENZENEBORONIC ACID N-METHYLDIETHANOLAMINE CYCLIC ESTER

Example 35
Commercially Available Compound
2-(3,5-DIFLUOROPHENYL)-5,5-DIMETHYL-1,3,2-DIOXABORINANE

Example 36
Commercially Available Compound
3-BROMOBENZENEBORONIC ACID N-METHYLDIETHANOLAMINE CYCLIC ESTER

Example 37
Commercially Available Compound
2-(4-BROMOPHENYL)-5,5-DIMETHYL-1,3,2-DIOXABORINANE

Example 38
Commercially Available Compound
2-(2-chloroPHENYL)-5,5-DIMETHYL-1,3,2-DIOXABORINANE

Example 39
Commercially Available Compound
2-(5,5-Dimethyl-[1,3,2]dioxaborinan-2-yl)-benzonitrile

Example 40
Commercially Available Compound
2-(2-Fluoro-phenyl)-5,5-dimethyl-[1,3,2]dioxaborinane

Example 42
Commercially Available Compound
2-(5,5-Dimethyl-[1,3,2]dioxaborinan-2-yl)-benzoic acid ethyl ester

Example 43
Commercially Available Compound
5-CHLORO-2-METHOXYPHENYLBORONIC ACID

Example 44
Commercially Available Compound
3,5-Dibromophenylboronic acid

Example 45
Commercially Available Compound
3-Ethoxyphenylboronic acid

Example 46
Commercially Available Compound
3-phenylphenylboronic acid

Example 47
Commercially Available Compound
4-fluorophenylboronic acid

Example 48
Commercially Available Compound
2-Bromophenylboronic acid

Example 49
Commercially Available Compound
3-Bromophenylboronic acid

Example 50
Commercially Available Compound
2,6-Dichlorophenylboronic acid

Example 51
Commercially Available Compound
3-Methylphenylboronic acid

Example 52
Commercially Available Compound
2-Chlorophenylboronic acid

Example 53
Commercially Available Compound
3-Chlorophenylboronic acid
3-(TRIFLUOROMETHOXY)BENZENEBORONIC ACID

Example 55
Commercially Available Compound
3-Trifluoromethylphenylboronic acid

Example 56
Commercially Available Compound
3,5-Bis(Trifluoromethyl)phenylboronic acid

Example 57
Commercially Available Compound
3,5-Dichlorophenylboronic acid

Example 58
Commercially Available Compound
3-Chloro-4-fluorophenylboronic acid

Example 59
Commercially Available Compound
3,5-Difluorophenylboronic acid

Example 60
Commercially Available Compound
3-Fluorophenylboronic acid

Example 61
Commercially Available Compound
2,3-DIFLUORO-4-PENTYLPHENYLBORONIC ACID

Example 62
Commercially Available Compound
3-FLUORO-4-BENZYLOXYPHENYL)BORONIC ACID

Example 63
Commercially Available Compound
3,4,5-Trifluorophenylboronic acid

Example 64
Commercially Available Compound
2,3,5-Trichlorophenylboronic acid

Example 65
Commercially Available Compound
2,5-Dichlorophenylboronic acid

Example 66
Commercially Available Compound
2,3-Difluorophenylboronic acid

Example 67
Commercially Available Compound
2,5-Difluorophenylboronic acid

Example 68
Commercially Available Compound
4'-(4,4,5,5-TETRAMETHYL-1,3,2-DIOXABOROLAN-2-YL)ACETANILIDE

Example 69
Commercially Available Compound
3,4-Difluorophenylboronic acid

Example 70
Commercially Available Compound
2,3-Dichlorophenylboronic acid

Example 71
Commercially Available Compound
2,3-Difluoro-4-bromophenylboronic acid

Example 72
Commercially Available Compound
3-Fluoro-4-phenylboronic acid

Example 73
Commercially Available Compound
2-Methoxy5-fluorophenylboronic acid

Example 74
Commercially Available Compound
3,4-Dichlorophenylboronic acid

Example 75
Commercially Available Compound
5-INDOLYL BORONIC ACID

Example 76
Commercially Available Compound
3-Formylphenylboronic acid

Example 77
Commercially Available Compound
4-(N,N-DIMETHYLCARBAMOYL)PHENYLBORONIC ACID

Example 78
Commercially Available Compound
6-Methoxy-2-phenyl-hexahydro-pyrano[3,2-a][1,3,2]dioxaborinine-7,8-diol

Example 79
Commercially Available Compound
2-Fluoro-4-(5-pentyl-[1,3,2]dioxaborinan-2-yl)-benzoic acid

Example 80
Commercially Available Compound
4-(3-Iodo-phenoxymethyl)-2-phenyl-[1,3,2]dioxaborolane

Example 81
Commercially Available Compound
3'-(4,4,5,5-TETRAMETHYL-1,3,2-DIOXABOROLAN-2-YL)-2-trimethylsilylthiophen

Example 82
Commercially Available Compound
4'-(4,4,5,5-TETRAMETHYL-1,3,2-DIOXABOROLAN-2-YL)2-nitrothiophene

Example 83
Commercially Available Compound
1-BENZOTHIOPHEN-3-YLBORONIC ACID

Example 84
Commercially Available Compound
2-FORMYL-3-THIOPHENEBORONIC ACID

Example 85
Commercially Available Compound
2-THIEN-3-YL-1,3,2-BENZODIOXABOROLE

Example 86
Commercially Available Compound
3-Thiophenboronic acid

Example 87
Commercially Available Compound
2-(2-FORMYL-3-METHYLTHIEN-5-YL)-1,3,2-DIOXABORINANE

Example 88
Commercially Available Compound
4-METHYLTHIOPHENE-2-BORONIC ACID

Example 89
Commercially Available Compound
5-METHYLFURAN-2-BORONIC ACID

Example 90
Commercially Available Compound
5-Methylthiophene-2-boronic acid

Example 91
Commercially Available Compound
BENZO[B]FURAN-2-BORONIC ACID

Example 92
Commercially Available Compound
Benzo[B]thiophene-2-boronic acid

Example 93
Commercially Available Compound
Furan-2-boronic acid

Example 94
Commercially Available Compound
5-Chlorothiophene-2-boronic acid

Example 95
Commercially Available Compound
5-Cyanothiophene-2-boronic acid

Example 96

Commercially Available Compound

5-Acetylthiophene-2-boronic acid

Example 97

Commercially Available Compound

Thiophene-2-boronic acid

Example 98

Commercially Available Compound

3-Bromothiophene-2-boronic acid

Example 99

Commercially Available Compound 5,5-Dimethyl-2-(3-iodothiophen-2-yl)-[1,3,2]dioxaborinane

Pharmacological Methods 3180.2: Assay for determination of percent inhibition by compound at 10 µM concentration.

A lipid emulsion with $^3$H-Triolein and phospholipid is used as substrate with a standard cencentration of highly purified HSL. BSA is added as product receptor. The substrate is prepared as follows:

30 µl PC:PI (20 mg/ml solution of PC:PI 3:1 prepared in chloroform)+128 µl cold TO+15 µl $^3$H-TO are mixed and then evaporated under a gentle stream of $N_2$ followed by 20–30 minutes in a Speedvac to ensure the absence of residual solvent.

Compound and HSL are incubated for 30 min at 25° C. before addition of substrate. Reaction is stopped after 30 min at 25° C. by adding a mixture of methanol, chloroform and heptane at high pH. Formed product is separated from substrate by phase separation.

Results are given as percent activity relative to an un-inhibited sample (no compound).

3190.1: Assay for determination of percent inhibition of hormone sensitive lipase by compound at 10 µM sample concentration.

A lipid emulsion with fluorochrome-labeled triacylglyceride and phospholipid is used as substrate with a standard concentration of highly purified HSL (12 µg/mL initial concentration corresponding to 600 ng/mL final concentration). BSA is added as product receptor. The transfer of the fluorochrome from the lipid phase to the water (BSA) phase changes the fluorescent properties of the fluorochrome. The changes can be monitored on a fluorimeter with an excitation wavelength of 450 nm and an emission wavelength of 545 nm.

Compound and HSL (2 µL compound, 10 µL enzyme and 70 µL PED-BSA buffer) is pre-incubated for 30 min at 25° C. before addition of substrate (100 µL). Amount of formed product is measured after 120 min incubation at 37° C.

Results are given as percent activity relative to a non-inhibited sample (no compound).

3180.1: Assay for determination of inhibitor $IC_{50}$ values.

A lipid emulsion with $^3$H-Triolein and phospholipid is used as substrate with a standard cencentration of highly purified HSL. BSA is added as product receptor. The substrate is prepared as follows:

30 µl PC:PI (20 mg/ml solution of PC:PI 3:1 prepared in chloroform)+128 µl cold TO+15 µl $^3$H-TO are mixed and then evaporated under a gentle stream of $N_2$ followed by 20–30 minutes in a Speedvac to ensure the absence of residual solvent.

Compound and HSL are incubated for 30 min at 25° C. before addition of substrate. Reaction is stopped after 30 min at 25° C. by adding a mixture of methanol, chloroform and heptane at high pH. Formed product is separated from substrate by phase separation.

Standard concentrations of compound are 100 µM, 20 µM, 4 µM, 0.8 µM, 0.16 µM and 0.032 µM (sample concentrations).

Results are given as $IC_{50}$ values after 4PL fit of obtained activity data.

3190.2: Assay for determination of $IC_{50}$ value for the inhibition of hormone sensitive lipase by compound. Standard concentrations of compound are 100µM and 5-fold dilutions (initial concentration corresponding to 10 µM final concentration and 5-fold).

A lipid emulsion with fluorochrome-labeled triacylglyceride and phospholipid is used as substrate with a standard concentration of highly purified HSL (12 µg/mL initial concentration corresponding to 600 ng/mL final concentration). BSA is added as product receptor. The transfer of the fluorochrome from the lipid phase to the water (BSA) phase changes the fluorescent properties of the fluorochrome. The changes can be monitored on a fluorimeter with an excitation wavelength of 450 nm and an emission wavelength of 545 nm.

Compound and HSL (20 µL compound, 10 µL enzyme and 70 µL PED-BSA buffer) is preincubated for 30 min at 25° C. before addition of substrate (100 µL). Amount of formed product is measured after 120 min incubation at 37° C.

Results are given as $IC_{50}$ values after 4PL fit of obtained activity data.

| COMPOUND ACCORDING TO EXAMPLE # | TEST 3190.1 HSL-FL Activity (%) | TEST 3180.2 HSL Activity (%) |
|---|---|---|
| 1 | 17 | |
| 2 | 17 | |
| 3 | 19 | |
| 4 | 32 | |
| 5 | 34 | |
| 6 | 36 | |
| 7 | 80 | |
| 8 | 29 | |
| 9 | 32 | |
| 10 | 39 | |
| 11 | 31 | |
| 12 | 39 | |
| 13 | 26 | |
| 14 | 40 | |
| 15 | 39 | |
| 16 | 61 | |
| 17 | 11 | |
| 18 | 43 | |
| 19 | 49 | |
| 20 | 27 | |
| 21 | 42 | |
| 22 | 31 | |
| 23 | 46 | |
| 24 | 58 | |
| 25 | 28 | |
| 27 | 29 | |
| 28 | 43 | |

-continued

| COMPOUND ACCORDING TO EXAMPLE # | TEST 3190.1 HSL-FL Activity (%) | TEST 3180.2 HSL Activity (%) |
|---|---|---|
| 29 | 36 | |
| 30 | 40 | |
| 31 | 27 | |
| 32 | 52 | |
| 33 | | 85 |
| 34 | | 81 |
| 35 | | 38 |
| 36 | | 43 |
| 37 | | 83 |
| 38 | | 89 |
| 39 | | 97 |
| 40 | | 68 |
| 42 | | 93 |
| 43 | | 36 |
| 44 | | 71 |
| 45 | | 90 |
| 46 | | 96 |
| 47 | | 65 |
| 48 | | 81 |
| 49 | | 33 |
| 50 | | 88 |
| 51 | | 64 |
| 52 | | 86 |
| 53 | | 34 |
| 54 | | 27 |
| 55 | | 21 |
| 56 | | 89 |
| 57 | | 46 |
| 58 | | 35 |
| 59 | | 25 |
| 60 | | 47 |
| 61 | | 85 |
| 62 | | 93 |
| 63 | | 26 |
| 64 | | 76 |
| 65 | | 55 |
| 66 | | 55 |
| 67 | | 34 |
| 68 | | 86 |
| 69 | | 45 |
| 70 | | 66 |
| 71 | | 61 |
| 72 | | 97 |
| 73 | | 62 |
| 74 | 53 | |
| 75 | 100 | |
| 76 | 80 | |
| 77 | 98 | |
| 78 | | 82 |
| 79 | | 100 |
| 80 | | 80 |
| 81 | | 85 |
| 82 | | 96 |
| 83 | | 76 |
| 84 | | 92 |
| 85 | | 89 |
| 87 | | 75 |
| 88 | | 49 |
| 89 | | 87 |
| 90 | | 48 |
| 91 | | 57 |
| 92 | | 53 |
| 93 | | 89 |
| 94 | | 17 |
| 95 | | 49 |
| 96 | | 68 |
| 97 | | 66 |
| 98 | | 84 |

What is claimed is:

1. A method of:

in a patient comprising, administering to a patient in need of such treatment a therapeutically effective amount of a boronic acid, an ester thereof, a prodrug thereof, wherein the boronic acid, an ester thereof or a prodrug thereof is of the general formula I

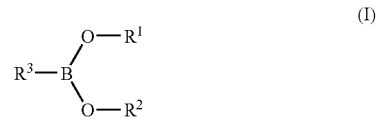

(I)

wherein $R^1$ and $R^2$ are independently selected from hydrogen, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl;

wherein $R^2$ is optionally covalently bound to $R^1$ by one or two ether, thioether, B, O—B, C—C, C=C or C—N bonds, to form a ring system with the O-atoms to which $R^1$ and $R^2$ are bound, said ring system may optionally form a fused ring system with benzene; and $R^3$ is selected from $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl, wherein each of hydroxy, sulfanyl, sulfonyl, sulfinyl, amino, imino, silyl, boranyl, C₁₋₆-alkyl, C₂₋₆-alkenyl, C₂₋₆-alkynyl, aryl, heteroaryl, C₃₋₈-heterocyclyl and C₃₋₈-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl, wherein each of hydroxy, sulfanyl, sulfonyl, sulfinyl, amino, imino, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl, wherein each of hydroxy, sulfanyl, sulfonyl, sulfinyl, amino, imino, silyl, boranyl, C₁₋₆-alkyl, C₂₋₆-alkenyl, C₂₋₆-alkynyl, aryl, heteroaryl, C₃₋₈-heterocyclyl, and C₃₋₁₀-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl, wherein each of hydroxy, sulfanyl, sulfonyl, sulfinyl, amino, imino, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl, wherein each of hydroxy, sulfanyl, sulfonyl, sulfinyl, amino, imino, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, C₁₋₆-alkyl, C₂₋₆-alkenyl, C₂₋₆-alkynyl, aryl, heteroaryl, C₃₋₈-heterocyclyl and C₃₋₁₀-cycloalkyl;

or any tautomeric forms, stereoisomers, mixture of stereoisomers including a racemic mixture, oligomers or polymorphs, or a pharmaceutically acceptable salt thereof, or a pharmaceutically acceptable solvate thereof.

2. The method according to claim 1, wherein the pK$_a$ of said boronic acid, an ester thereof, a prodrug thereof or a pharmaceutically acceptable salt thereof is between 2.0 and 11.5.

3. The method according to claim 1, wherein the boronic acid, an ester thereof or a prodrug thereof is a dimer or trimer of a boronic acid.

4. The method according to claim 3, wherein said dimer or trimer of the boronic acid comprises a structure selected from:

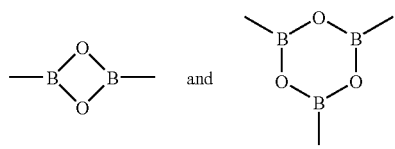

5. The use according to claim 1, wherein the boronic acid, an ester thereof, or a prodrug thereof, comprises a structure selected from the group consisting of

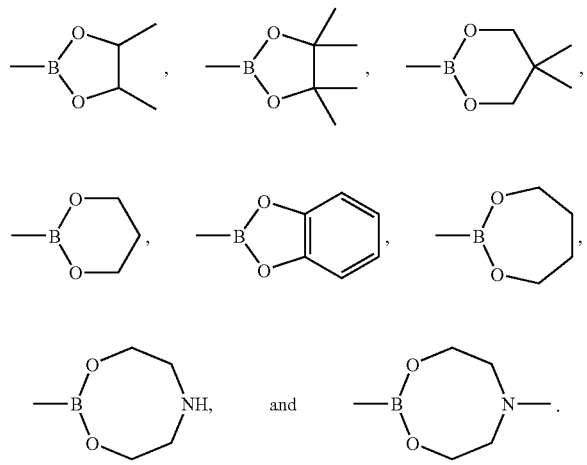

6. The use according to claim 1, wherein the group R³ in the general formula (I) comprises an optionally substituted moiety selected from the group consisting of pyrrolidine-2-yl, pyrrolidine-3-yl, pyrrole-2-yl, pyrrole-3-yl, 3H-pyrrole-2-yl, 3H-pyrrole-3-yl, 3H-pyrrole-4-yl, 3H-pyrrole-5-yl, oxolane-2-yl, oxolane-3-yl, furane-2-yl, furane-3-yl, thiolane-2-yl, thiolane-3-yl, thiophene-2-yl, thiophene-3-yl, pyrazole-3-yl, pyrazole-4-yl, pyrazole-5-yl, pyrazolidine-3-yl, pyrazolidine-4-yl, imidazole-2-yl, imidazole-4-yl, imidazole-5-yl, imidazolidine-2-yl, imidazolidine-4-yl, 3H-pyrazole-3-yl, 3H-pyrazole-4-yl, 3H-pyrazole-5-yl, isoxazole-3-yl, isoxazole-4-yl, isoxazole-5-yl, oxazole-2-yl, oxazole-4-yl, oxazole-5-yl, isothiazole-3-yl, isothiazole-4-yl, isothiazole-5-yl, thiazole-2-yl, thiazole-4-yl, thiazole-5-yl, 1,2,5-oxadiazole-3-yl, 1,3,5-oxadiazole-2-yl, 1,3,5-oxadiazole-4-yl, 1,3,4-oxadiazole-2-yl, 1,2,3,5-oxatriazole-4-yl, 1,2,5-thiadiazole-3-yl, 1,3,5-thiadiazole-2-yl, 1,3,5-thiadiazole-4-yl, 1,3,4-thiadiazole-2-yl, 1,2,3,5-thiatriazole-4-yl, 1,2,3-triazole-4-yl, 1,2,3-triazole-5-yl, 1,2,4-triazole-3-yl, 1,2,4-triazole-5-yl, 1,2,5-triazole-3-yl, tetrazole-5-yl, 1,3-oxathiole-2-yl, 1,3-oxathiole-4-yl, 1,3-oxathiole-5-yl, benzofurane-2-yl, benzofurane-3-yl, isobenzofurane-1-yl, benzothiophene-2-yl, benzothiophene-3-yl, isobenzothiophene-1-yl, 1H-indole-2-yl, 1H-indole-3-yl, 2H-isoindole-1-yl, indolizine-1-yl, indolizine-2-yl, indolizine-3-yl, 1H-benzimidazole-2-yl, 1H-benzothiazole-2-yl, 1H-benzoxazole-2-yl, 1H-benzisooxazole-3-yl, 3H-indazole-3-yl, piperedine-1-yl, piperedine-2-yl, piperedine-3-yl, piperedine-4-yl, piperazine-1-yl, piperazine-2-yl, 2,5-dione-piparazine-1-yl, 2,5-dione-piparazine-3-yl and phenyl.

7. The method according to claim 1, wherein the group R³ is selected from the group consisting of:

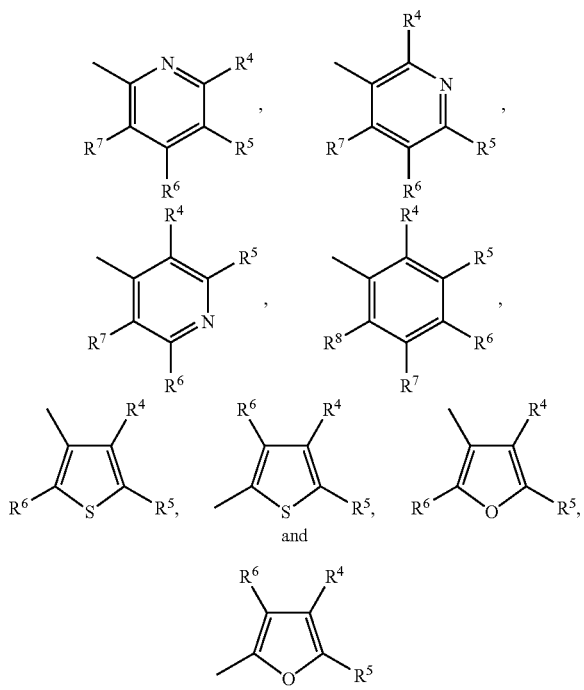

wherein $R^4$, $R^5$, $R^6$, $R^7$ and $R^8$ are independently selected from $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl, wherein each of hydroxy, sulfanyl, sulfonyl, sulfinyl, amino, imino, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl is optionally substituted with one or more substituents independently selected from hydroxy, sulfanyl, sulfonyl, sulfinyl, oxo, thioxo, halogen, amino, imino, cyano, nitro, silyl, boranyl, $C_{1-6}$-alkyl, $C_{2-6}$-alkenyl, $C_{2-6}$-alkynyl, aryl, heteroaryl, $C_{3-8}$-heterocyclyl and $C_{3-10}$-cycloalkyl.

8. The method according to claim 7, wherein the molar weight of each of $R^4$, $R^5$, $R^6$, $R^7$ and $R^8$ are below about 100 Dalton.

9. The method according to claim 7, wherein $R^4$, $R^5$, $R^6$, $R^7$ and $R^8$ are independently selected from hydrogen, halogen, hydroxyl, perhalomethyl, perhalomethoxy, $C_{1-6}$-alkyl, $C_{1-6}$-alkoxy and $C_{1-6}$-alkylthio.

10. The method according to claim 7, wherein $R^4$, $R^5$, $R^6$, $R^7$ and $R^8$ are independently selected from hydrogen, halogen, methyl, methoxy, thiomethoxy, perhalomethyl, perhalomethoxy.

11. The method according to claim 7, wherein $R^4$, $R^5$, $R^6$, $R^7$ and $R^8$ are independently selected from hydrogen, halogen, trifluoromethyl and trifluoromethoxy.

12. The method according to claim 1, wherein the group $R^1$ is H.

13. The method according to claim 1, wherein the group $R^1$ is H and the group $R^2$ is H.

14. The method according to claim 1, wherein said boronic acid, an ester thereof or a prodrug thereof is selected from the group consisting of:

2-(5-Chlorothiophen-2-yl)-4,4,5,5-tetramethyl-[1,3,2] dioxaborolane, 2-(5-Chlorothiophen-2-yl)-5,5-dimethyl-[1,3,2] dioxaborinane, 2-(5-Chlorothiophen-2-yl)-[1,3,6,2]dioxazaborocane, 2-(3,5-Difluorophenyl)-[1,3,6,2]dioxazaborocane, 2-(3-Bromophenyl)-[1,3,6,2]dioxazaborocane, 2-(3-Chlorophenyl)-[1,3,6,2]dioxazaborocane, 2-(3-Fluorophenyl)-[1,3,6,2]dioxazaborocane, 2-(3-Trifluoromethylphenyl)-[1,3,6,2]dioxazaborocane, 2-(3,4,5-Trifluorophenyl)-[1,3,6,2]dioxazaborocane, 2-(3-Chlorophenyl)-5,5-dimethyl-[1,3,2]dioxaborinane, 5,5-Dimethyl-2-(3-trifluoromethylphenyl)-[1,3,2] dioxaborinane, 2-(5-Chloro-2-methoxyphenyl)-[1,3,6,2] dioxazaborocane, 2-(3-Trifluoromethoxyphenyl)-[1,3,6,2]dioxazaborocane, 2-(3,5-Dichlorophenyl)-[1,3,6,2]dioxazaborocane, 2-(3-Chloro-4-fluorophenyl)-[1,3,6,2]dioxazaborocane, 2-(4-Methylthiophen-2-yl)-[1,3,6,2]dioxazaborocane, 2-(3-Bromophenyl)-5,5-dimethyl-[1,3,2]dioxaborinane, 2-(5-Chloro-2-methoxyphenyl)-5,5-dimethyl-[1,3,2] dioxaborinane, 5,5-Dimethyl-2-(3,4,5-trifluorophenyl)-[1,3,2] dioxaborinane, 5,5-Dimethyl-2-(3-trifluoromethoxyphenyl)-[1,3,2] dioxaborinane, 2-(3,5-Dichlorophenyl)-5,5-dimethyl-[1,3,2] dioxaborinane, 2-(3-Chloro-4-fluorophenyl)-5,5-dimethyl-[1,3,2] dioxaborinane, 2-(3-Fluorophenyl)-5,5-dimethyl-[1,3,2]dioxaborinane, 5,5-Dimethyl-2-(4-methylthiophen-2-yl)-[1,3,2] dioxaborinane, 2-(3-Bromophenyl)-4,4,5,5-tetramethyl-[1,3,2] dioxaborolane, 2-(5-Chloro-2-methoxyphenyl)-4,4,5,5-tetramethyl-[1,3,2]dioxaborolane,
4,4,5,5-Tetramethyl-2-(3-trifluoromethoxyphenyl)-[1,3,2]dioxaborolane,
2-(3,5-Dichlorophenyl)-4,4,5,5-tetramethyl-[1,3,2]dioxaborolane,
2-(3-Chloro-4-fluorophenyl)-4,4,5,5-tetramethyl-[1,3,2]dioxaborolane,
2-(3-Chlorophenyl)-4,4,5,5-tetramethyl-[1,3,2]dioxaborolane,
4,4,5,5-Tetramethyl-2-(3-trifluoromethylphenyl)-[1,3,2]dioxaborolane,
4,4,5,5-Tetramethyl-2-(4-methylthiophen-2-yl)-[1,3,2]dioxaborolane,
4-Benzyloxyphenylboronic acid,
4-Bromobenzeneboronic acid n-methyldiethanolamine cyclic ester,
2-(3,5-Difluorophenyl)-5,5-dimethyl-1,3,2-dioxaborinane,3-Bromobenzeneboronic acid n-methyldiethanolamine cyclic ester,
2-(4-Bromophenyl)-5,5-dimethyl-1,3,2-dioxaborinane,
2-(2-Chlorophenyl)-5,5-dimethyl-1,3,2-dioxaborinane,
2-(5,5-Dimethyl-[1,3,2]dioxaborinan-2-yl)-benzonitrile,
2-(2-Fluoro-phenyl)-5,5-dimethyl-[1,3,2]dioxaborinane,
2-(5,5-Dimethyl-[1,3,2]dioxaborinan-2-yl)-benzoic acid ethyl ester,
5-Chloro-2-methoxyphenylboronic acid,
3,5-Dibromophenylboronic acid,
3-Ethoxyphenylboronic acid,
3-phenylphenylboronic acid,
4-fluorophenylboronic acid,
2-Bromophenylboronic acid,
3-Bromophenylboronic acid,
2,6-Dichlorophenylboronic acid,
3-Methylphenylboronic acid,
2-Chlorophenylboronic acid,
3-Chlorophenylboronic acid,
3-(Trifluoromethoxy)benzeneboronic acid,
3-Trifluoromethylphenylboronic acid,
3,5-Bis(Trifluoromethyl)phenylboronic acid,
3,5-Dichlorophenylboronic acid,
3-Chloro-4-fluorophenylboronic acid,
3,5-Difluorophenylboronic acid,
3-Fluorophenylboronic acid,
2,3-Difluoro-4-pentylphenylboronic acid,
(3-Dluoro-4-benzyloxyphenyl)boronic acid,
3,4,5-Trifluorophenylboronic acid,
2,3,5-Trichlorophenylboronic acid,
2,5-Dichlorophenylboronic acid,
2,3-Difluorophenylboronic acid,
2,5-Difluorophenylboronic acid,
4'-(4,4,5,5-Tetramethyl-1,3,2-dioxaborolan-2-yl) acetanilide,
3,4-Difluorophenylboronic acid,
2,3-Dichlorophenyiboronic acid,
2,3-Difluoro-4-bromophenylboronic acid,
3-Fluoro-4-phenylboronic acid,
2-Methoxy5-fluorophenylboronic acid,
3,4-Dichlorophenylboronic acid,
5-Indolyl boronic acid,
3-Formylphenylboronic acid,
4-(N,N-dimethylcarbamoyl)phenylboronic acid,
6-Methoxy-2-phenyl-hexahydro-pyrano[3,2-a][1,3,2]dioxaborinine-7,8-diol,
2-Fluoro-4-(5-pentyl-[1,3,2]dioxaborinan-2-yl)-benzoic acid,
4-(3-Iodo-phenoxymethyl)-2-phenyl-[1,3,2]dioxaborolane,
3'-(4,4,5,5-Tetramethyl-1,3,2-dioxaborolan-2-yl)-2-trimethylsilylthiophen,
4'-(4,4,5,5-Tetramethyl-1,3,2-dioxaborolan-2-yl)2-nitrothiophene,
1-Benzothiophen-3-ylboronic acid,
2-Formyl-3-thipheneboronic acid,
2-Thien-3-yl-1,3,2-benzodioxaborole,
3-Thiophenboronic acid,
2-(2-Formyl-3-methylthien-5-yl)-1,3,2-dioxaborinane,
4-Methylthiophene-2-boronic acid,
5-Methylfuran-2-boronic acid,
5-Methylthiophene-2-boronic acid,
Benzo[b]furan-2-boronic acid,
Benzo[B]thiophene-2-boronic acid,
Furan-2-boronic acid,
5Chlorothiophene-2-boronic acid,
5-Cyanothiophene-2-boronic acid,
5-Acetylthiophene-2-boronic acid,
Thiophene-2-boronic acid,
3-Bromothiophene-2-boronic acid, and
5,5-Dimethyl-2-(3-iodothiophen-2-yl)-[1,3,2]dioxaboinane.

15. The method according to claim 2, wherein the compound is $R^3$-B(OH)$_2$ and the $pK_a$ of the $R^3$ substituent is between 2.0 and 11.5.

16. The method according to claim 1, wherein said boronic acid, or an ester thereof or a prodrug thereof has a molar weight of no greater than 1000 D.

17. The method according to claim 1, wherein the molar weight of said boronic acid, an ester thereof or a prodrug thereof is less than 750 D.

18. The method according to claim 1, wherein said boronic acid, an ester thereof or a prodrug thereof has an $IC_{50}$ value as determined by the assay 3190.2 or 3180.1 disclosed herein of less than 50 µM.

19. The method according to claim 1, wherein said boronic acid, an ester thereof or a prodrug thereof has a solubility in water at 25° C. and pH 2.0 of at least 0.5 mg/L.

20. The method according to claim 1, wherein administration of said boronic acid, an ester thereof or a prodrug thereof is by the oral, nasal, transdermal, pulmonal, or parenteral route.

21. The method according to claim 1, wherein a pharmaceutical composition is administered, said pharmaceutical composition comprising, as an active ingredient, a boronic acid, an ester thereof, a prodrug thereof, or a pharmaceutically acceptable salt thereof, or a pharmaceutically acceptable solvate thereof, together with a pharmaceutically acceptable carrier or diluent.

22. The method according to claim 2, wherein a pharmaceutical composition is administered, said pharmaceutical composition comprising, as an active ingredient, a boronic acid, an ester thereof or a prodrug thereof, or a pharmaceutically acceptable salt thereof, together with a pharmaceutically acceptable carrier or diluent.

23. The pharmaceutical composition according to claim 22 wherein the pharmaceutical composition in unit dosage form, comprising from about 0.05 mg to about 2000 mg, preferably from about 0.1 to about 500 mg of the boronic acid, an ester thereof, a prodrug thereof or a pharmaceutically acceptable salt thereof or a pharmaceutically acceptable solvate thereof.

24. The pharmaceutical composition according to claim 21 is wherein the pharmaceulical composition for oral, nasal, transdermal, pulmonal or parenteral administration.

25. The method according to claim 25, wherein said disorder is selected from the group consisting of insulin resistance, diabetes type 1, diabetes type 2, metabolic syndrome X, impaired glucose tolerance, hyperglycemia, dyslipidemia, obesity, abnormalities of lipoprotein metabolism and any combination thereof.

26. A method of treating a patient suffering from insulin resistance, diabetes type 1, diabetes type 2, metabolic syndrome X, impaired glucose tolerance, hyperglycemia, dyslipidemia, hyperlipoproteinemia, hypertriglyceridemia, hyperlipidemia, hypercholesterolemia, or other abnormalities of lipoprotein metabolism, said method comprising administering to a patient in need thereof a pharmaceutically effective amount of a boronic acid according to claim 1, an ester thereof, a prodrug thereof or a pharmaceutically acceptable salt thereof or a pharmaceutically acceptable solvate thereof.

27. The method according to claim 29, wherein the $pK_a$ of said boronic acid, an ester thereof, a prodrug thereof or a pharmaceutically acceptable salt thereof is between 2.0 and 11.5.

28. The method according to claim 29, wherein the patient is treated with said boronic acid, an ester thereof, a prodrug thereof or a pharmaceutically acceptable salt thereof or a pharmaceutically acceptable solvate thereof for at least about 1 week, for at least about 2 weeks, for at least about 4 weeks, for at least about 2 months or for at least about 4 months.

29. The method according to claim 2, wherein the $pK_a$ of said boronic acid, an ester thereof, a prodrug thereof or a pharmaceutically acceptable salt thereof is between 3.0 and 10.5.

30. The method according to claim 2, wherein the $pK_a$ of said boronic acid, an ester thereof, a prodrug thereof or a pharmaceutically acceptable salt thereof is between 4.0 and 9.5.

31. The method according to claim 2, wherein the $pK_a$ of said boronic acid, an ester thereof, a prodrug thereof or a pharmaceutically acceptable salt thereof is between 5.0 and 8.5.

32. The method according to claim 2, wherein the $pK_a$ of said boronic acid, an ester thereof, a prodrug thereof or a pharmaceutically acceptable salt thereof is between 5.5 and 8.0.

33. The method according to claim 2, wherein the $pK_a$ of said boronic acid, an ester thereof, a prodrug thereof or a pharmaceutically acceptable salt thereof is between 6.0 and 7.5.

34. The method according to claim 8, wherein the molar weight of each of $R^4$, $R^5$, $R^6$, $R^7$ and $R^8$ is below about 80 Dalton.

35. The method according to claim 8, wherein the molar weight of each of $R^4$, $R^5$, $R^6$, $R^7$ and $R^8$ is below 50 Dalton.

36. The method according to claim 8, wherein the molar weight of each of $R^4$, $R^5$, $R^6$, $R^7$ and $R^8$ is below about 20 Dalton.

37. The method according to claim 15, wherein the compound is $R^3\text{-B(OH)}_2$ and the $pK_a$ of the $R^3$ substituent is between 3.0 and 10.5.

38. The method according to claim 15, wherein the compound is $R^3\text{-B(OH)}_2$ and the $pK_a$ of the $R^3$ substituent is between 4.0 and 9.5.

39. The method according to claim 15, wherein the compound is $R^3\text{-B(OH)}_2$ and the $pK_a$ of the $R^3$ substituent is between 5.0 and 8.5.

40. The method according to claim 15, wherein the compound is $R^3\text{-B(OH)}_2$ and the $pK_a$ of the $R^3$ substituent is between 5.5 and 8.0.

41. The method according to claim 15, wherein the compound is $R^3\text{-B(OH)}_2$ and the $pK_a$ of the $R^3$ substituent is between 6.0 and 7.5.

42. The method according to claim 17, wherein the molar weight of said boronic acid, an ester thereof or a prodrug thereof is less than 500 D.

43. The method according to claim 17, wherein the molar weight of said boronic acid, an ester thereof or a prodrug thereof is less than 350 D.

44. The method according to claim 17, wherein the molar weight of said boronic acid, an ester thereof or a prodrug thereof is less than 300 D.

45. The method according to claim 17, wherein the molar weight of said boronic acid, an ester thereof or a prodrug thereof is less than 250 D.

46. The method according to claim 17, wherein the molar weight of said boronic acid, an ester thereof or a prodrug thereof is less than 200 D.

47. The method according to claim 18, wherein said boronic acid, an ester thereof or a prodrug thereof has an $IC_{50}$ value as determined by the assay 3190.2 or 3180.1 disclosed herein of less than 5 µM.

48. The method according to claim 18, wherein said boronic acid, an ester thereof or a prodrug thereof has an $IC_{50}$ value as determined by the assay 3190.2 or 3180.1 disclosed herein of less than 500 nM.

49. The method according to claim 18, wherein said boronic acid, an ester thereof or a prodrug thereof has an $IC_{50}$ value as determined by the assay 3190.2 or 3180.1 disclosed herein of less than 100 nM.

50. The method according to claim 19, wherein said boronic acid, an ester thereof or a prodrug thereof has a solubility in water at 25° C. and pH 2.0 of at least 2.5 mg/L.

51. The method according to claim 19, wherein said boronic acid, an ester thereof or a prodrug thereof has a solubility in water at 25° C. and pH 2.0 of at least 20 mg/L.

52. The method according to claim 19, wherein said boronic acid, an ester thereof or a prodrug thereof has a solubility in water at 25° C. and pH 2.0 of at least 200 mg/L.

53. The method according to claim 19, wherein said boronic acid, an ester thereof or a prodrug thereof has a solubility in water at 25° C. and pH 2.0 of at least 2 mg/L.

54. The pharmaceutical composition according to claim 23 wherein the pharmaceutical composition in unit dosage form, comprising from about 0.1 to about 500 mg of the boronic acid, an ester thereof, a prodrug thereof or a pharmaceutically acceptable salt thereof or a pharmaceutically acceptable solvate thereof.

55. The method according to claim 30, wherein the $pK_a$ of said boronic acid, an ester thereof, a prodrug thereof or a pharmaceutically acceptable salt thereof is between 3.0 and 10.5.

56. The method according to claim 30, wherein the $pK_a$ of said boronic acid, an ester thereof, a prodrug thereof or a pharmaceutically acceptable salt thereof is between 4.0 and 9.5.

57. The method according to claim 30, wherein the $pK_a$ of said boronic acid, an ester thereof, a prodrug thereof or a pharmaceutically acceptable salt thereof is between 5.0 and 8.5.

58. The method according to claim 30, wherein the $pK_a$ of said boronic acid, an ester thereof, a prodrug thereof or a pharmaceutically acceptable salt thereof is between 5.5 and 8.0.

59. The method according to claim 30, wherein the $pK_a$ of said boronic acid, an ester thereof, a prodrug thereof or a pharmaceutically acceptable salt thereof is between 6.0 and 7.5.

* * * * *